United States Patent [19]
Groger et al.

[11] Patent Number: 5,591,407
[45] Date of Patent: Jan. 7, 1997

[54] LASER DIODE SENSOR

[75] Inventors: Howard P. Groger, Gainesville, Fla.; Peter Lo, Blacksburg, Va.; Martin Weiss, New Port Richey; Peter Zory, Gainesville, both of Fla.

[73] Assignee: American Research Corporation of Virginia, Radford, Va.

[21] Appl. No.: 426,659

[22] Filed: Apr. 21, 1995

[51] Int. Cl.⁶ .................................................. G01N 21/63
[52] U.S. Cl. .................................. 422/82.05; 422/82.08; 422/82.11; 356/318
[58] Field of Search ...................... 257/253, 414; 372/44, 43; 436/172, 164; 422/82.05, 82.08, 82.07, 82.09, 82.11; 356/318

[56] References Cited

U.S. PATENT DOCUMENTS

| | | |
|---|---|---|
| 4,169,676 | 10/1979 | Kaiser . |
| 4,819,036 | 4/1989 | Kuroda ........................................ 357/4 |
| 4,844,613 | 7/1989 | Batchelder et al. . |
| 4,880,752 | 11/1989 | Keck et al. . |
| 4,894,833 | 1/1990 | Carlin ........................................ 372/44 |
| 5,047,213 | 9/1991 | Finlan et al. . |
| 5,107,316 | 4/1992 | Jelly ........................................... 357/25 |
| 5,109,386 | 4/1992 | Bradley ..................................... 372/32 |
| 5,132,097 | 7/1992 | Van Deusen et al. . |
| 5,194,393 | 3/1993 | Hugl et al. . |
| 5,208,878 | 5/1993 | Thulke ....................................... 385/14 |
| 5,212,099 | 5/1993 | Marcus . |
| 5,268,145 | 12/1993 | Namba et al. . |
| 5,298,428 | 3/1994 | O'Rourke et al. . |
| 5,298,741 | 3/1994 | Walt et al. . |
| 5,299,141 | 3/1994 | Hungerford et al. . |
| 5,308,771 | 5/1994 | Zhou et al. . |
| 5,315,673 | 5/1994 | Stetter ...................................... 385/12 |
| 5,317,897 | 6/1994 | Jelly ....................................... 73/31.06 |

OTHER PUBLICATIONS

Dai et al. Can. J. Phys. 70, 921 (1992).
Hunziker (AN 1995:138017) Abstract Only.
Hamao (AN 1993:263473) HCA Plus.
Tsang (AN 1995:77003) HCA Plus.
Wu et al., "Large Wavelength Shifts in Thin p–clad InGaAs QW Lasers", 3–page paper presented at IEEE/LEOS Annual Mtg Boston, MA (Nov. 1994).

*Primary Examiner*—Jeffrey Snay
*Attorney, Agent, or Firm*—James Creighton Wray

[57] ABSTRACT

A chemical sensor uses a semiconductor diode laser having a surface active region. A laser structure, including an active layer, a cladding layer, a barrier layer and a grating layer, is constructed on a substrate. A contact layer is deposited on a surface of the laser structure. One or more electrodes are positioned on the contact layer. A segmented electrode has a first contact pad, a second contact pad, and a surface active region between the first and second pads. A surface active region is created between the two electrodes. The tail of the lasing signal interacts with surface features of the diode laser or with chemical materials or probes in contact with the surface of the diode laser or in contact with coatings on the surface of the diode laser. Chemical changes in the ambient environment induce changes in the laser signal. The modified laser signal output is detected by a detector region integral with or separated from the laser structure. The laser diode sensor has applications in fields involving chemical sensing and identification, including automotive, environmental and medical fields.

33 Claims, 1 Drawing Sheet

U.S. Patent    Jan. 7, 1997    5,591,407
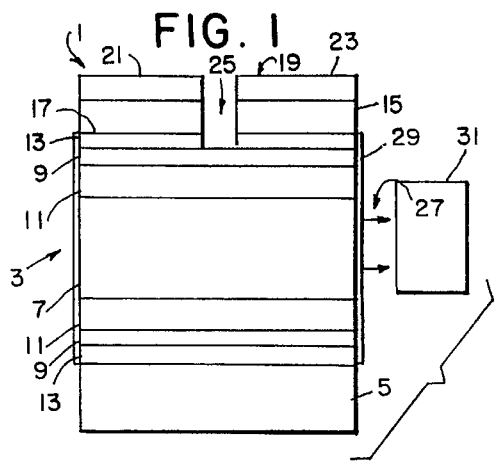
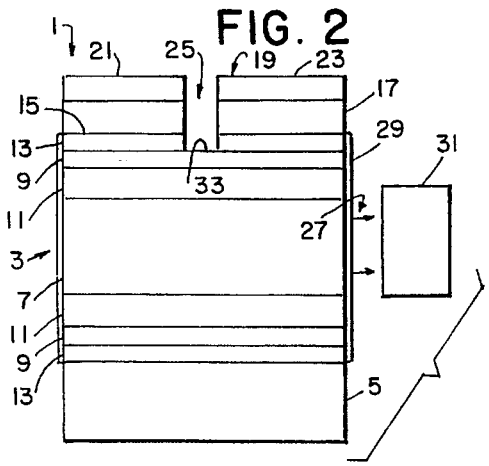
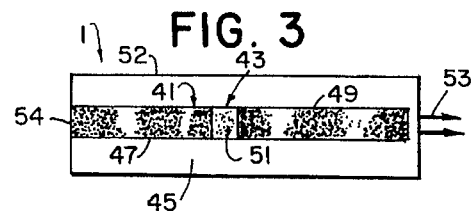
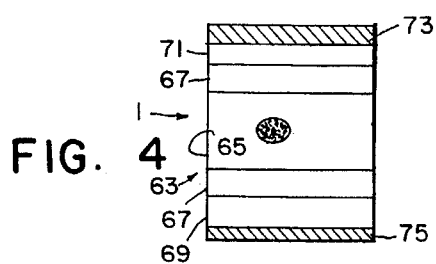
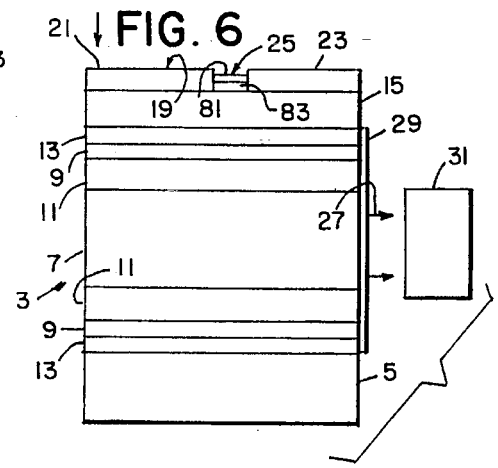
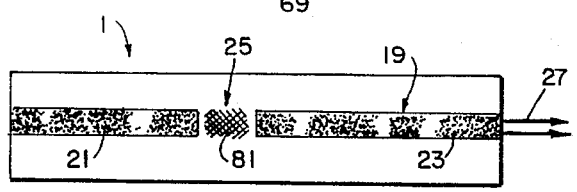
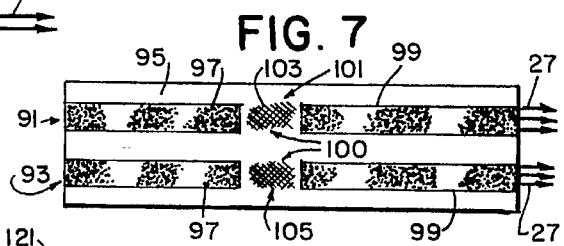
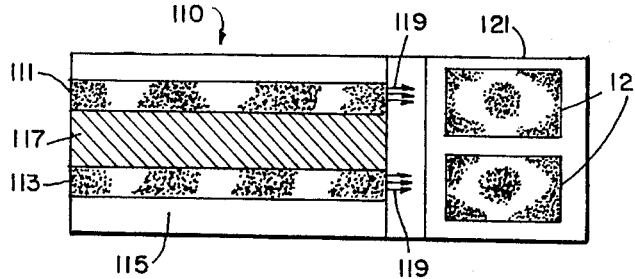

LASER DIODE SENSOR

BACKGROUND OF THE INVENTION

The present invention relates generally to sensors for detecting chemical changes in the ambient environment.

Chemical sensing and identification apparatus are implemented in many diverse fields. Automobile manufacturers use chemical sensors for measuring air/fuel ratios and intend to use sensors to measure pollutant emissions, alternative fuel quality and build-up of volatile chemicals such as hydrogen in battery-operated vehicles. Environmental testing firms and industries required to meet Federal Air Quality Standards and workplace safety standards use sensors to detect contaminant concentrations, toxic vapors and the distribution of pollutants in process control systems. Biomedical sensors are used to monitor concentrations of glucose, blood gases and other constituents in the blood and for detecting analytes such as hormones and toxins.

Existing sensors have proven inadequate. Existing sensors do not meet requirements of cost, accuracy, precision and instrument size necessary in many applications. Electrochemical sensors require reference channels, are prone to drift and have considerable accuracy and cost restraints. Acoustic sensors are currently under development but suffer from problems related to high excitation frequencies and lack of selectivity. Optical sensors are suitable for a wide range of applications. Unfortunately, the most sensitive optical methods can require costly coupling and interconnect components that reduce the range of suitable applications for which optical sensors may be an attractive option.

Needs exist for chemical sensors with high sensitivity, precision and amenability to low-cost production methods for use in environmental monitoring, in process control and in biomedical analysis.

SUMMARY OF THE INVENTION

The present invention answers the above needs through high sensitivity laser intracavity sensing on a low-cost diode laser structure. Chemical sensors based on semiconductor diode lasers having surface-active regions are disclosed. The output of the semiconductor diode laser is affected by the presence of an analyte or a probe for an analyte in contact with the surface or coating on the surface of a semiconductor diode laser that exhibits sensitivity to surface effects. In particular, surface-sensitive diode lasers are prepared using a suitable active layer, a reducing layer and a contact layer, such that in the region of surface sensitivity, the cladding layer has a thickness less than 0.5 microns and the thicknesses of the reducing layer and the contact layer are reduced. The "tail" of the lasing mode interacts with surface features of the diode laser or with chemical materials or probes in contact with the surface of the diode laser or in contact with thin coatings at the surface of the diode laser.

Changes in laser spectral output, laser threshold, laser intensity, laser modulation versus frequency, laser polarization, laser mode structure or laser speckle can be observed using photodiodes or array detectors external to the laser substrate or through changes in the current-voltage characteristics of the laser diode observed electronically. Similarly, if the probe is a fluorophore coupled to the laser diode surface or to a coating at the laser diode surface or to a waveguide coupled to the laser diode surface, the output fluorescence amplitude, decay or polarization can be detected by any means described above.

In the presence of specific chemical environments, the chemical materials in contact with the laser diode surface layer or a coating on the surface of the laser diode surface layer exhibit a change in linear or nonlinear refractive index, spectral optical density, spectral absorption, or other optical electrical or thermal properties measurable as a change in laser output. Optical signals emitted by the laser diode or by materials in contact with the laser diode are sensed by photodetectors or electronically as a change in current versus voltage characteristics of the laser diode. The laser diode chemical sensor may contain integrated optical or optoelectronic components as well as signal amplification or signal conditioning sections to provide output in direct proportion to the amount of analyte present.

In one embodiment of the present invention, a gallium indium phosphide laser is constructed on a suitable active layer, a barrier layer, a cladding layer, a reducing layer and a contact layer, such that in the region of surface sensitivity, the cladding layer has a thickness less than 0.5 microns and the thicknesses of the reducing layer and the contact layer are reduced, perhaps to where the reducing and contact layer are not present. The pads are separated by a distance of about 100 microns. A thin coating of silica, alumina or other insulator, measuring 5 nm to 50 nm in thickness, can be deposited over the contact pads and over the region of the laser surface between the contact pads. The region between the contact pads is surface-sensitive. In particular, when 1) the composition of the active region of the laser is selected so as to allow lasing within the 635 nm to 670 nm wavelength range, 2) a thin layer of nafion is deposited over the gap region between the two contact pads, and 3) the thin layer of nafion contains from 0.1 milliMolar to 1 milliMolar concentrations of oxazine 720, the resulting laser output is altered in the presence of ammonia vapor.

In a second embodiment of the present invention, the laser structure described in the first embodiment is designed to lase at a wavelength where the analyte of interest or a probe for the analyte of interest has an absorption peak. Interaction with the analyte in the laser cavity provides a change in the laser output. That change is dependent on the concentration of analyte material. For example, the probe may be a pH-sensitive dye such as bromothymol blue, bromcresol purple, methylene blue or other pH-sensitive material with absorption dependent on pH in the 635 nm to 850 nm wavelength range. The light output from the laser depends on the pH of the material in contact with the dye and its immobilization polymer. The use of an absorbing dye with pH dependence provides a sensitive indicator for ammonia, carbon dioxide and various acid vapors.

In a third embodiment, a gallium indium phosphide, gallium aluminum arsenide or gallium arsenide quantum well active layer or other active layer providing lasing output in the 635 nm to 850 nm wavelength range is fabricated on suitable substrate material. A barrier layer, a cladding layer, a reducing layer and a contact layer are positioned on top of the active layer designed to produce dual polarization lasing. Gold contact pads are deposited over the contact layer to form a segmented top electrode. In the region between the contact pads, the thickness of the cladding layer is less than 0.5 microns. Optimal thicknesses may be in the 0.1 to 0.2 micron range. The reducing layer and contact layers may not be present in the surface active region. Thin layers of silica, alumina or titania are deposited on the GaAs in the region between the contact pads to provide a buffer layer and a tuning layer. Those layers provide coupling to surface plasmon resonance produced when a thin, 30 nm to 50 nm gold layer is deposited in the region of the laser surface between the contact pads. Suitable maskings, depositions or etchings may be needed to avoid shorting of the laser surface. The region between the contact pads is surface sensitive in that the thin gold layer affects the polarization of the light exciting the laser structure. Coating the thin gold film in the region between the contact pads with a thin layer of nafion provides a chemically sensitive structure. When the laser structure has a Bragg grating operating as the ends of the optical cavity, a totally integrated surface plasmon resonance sensor is fashioned by constructing a polarization beamsplitter on the inactive region of the semiconductor structure between the exit Bragg grating and the point of emission from the laser. The polarization extinction ratio detected by two photodiodes provides an indication of surface plasmon resonance.

In a fourth embodiment, a gallium indium phosphide, gallium aluminum arsenide or gallium arsenide quantum well active layer or other active layer providing lasing output in the 635 nm to 850 nm wavelength range is fabricated on suitable substrate material. A barrier layer, a cladding layer, a reducing layer and a contact layer are positioned on top of the active layer. In the region of surface sensitivity, the cladding layer has a thickness less than 0.5 microns and the thicknesses of the reducing layer and the contact layer are reduced, perhaps to where the reducing and the contact layers are not present. Gold contact pads are deposited over the p+-GaAs contact layer to form a segmented top electrode. Thin layers of silica, alumina or titania are deposited on the GaAs in the region between the contact pads and overlaid with a fluorophore in a polymer, sol-gel or thin-film deposited binder. Fluorescence is quenched in materials deposited directly over the semiconductor layer or metal pad layer but is enhanced when a suitable interlayer is deposited. Fluorescence is generated as the "tail" of the lasing mode or modal structure interacts with the materials in the region between the pads. Fluorescence is detected by a photodetector with field-of-view at right angles to the fluorophore. The fluorescence decay time is detected as a change in the modulation characteristics of the diode laser.

In a fifth embodiment, a gallium indium phosphide, gallium aluminum arsenide or gallium arsenide quantum well active layer or other active layer providing lasing output in the 635 nm to 850 nm wavelength range is fabricated on suitable substrate material. A barrier layer, a cladding layer, a reducing layer and a contact layer are positioned on top of the active layer. In the region of surface sensitivity, the cladding layer has a thickness less than 0.5 microns and the thicknesses of the reducing layer and the contact layer are reduced, perhaps to where the reducing and the contact layers are not present. One gold contact pad is deposited over the contact layer to act as a top electrode such that there is an unpumped region of the structure. While that structure requires somewhat larger voltages to reach the lasing threshold, the single contact pad allows light generated by the laser to interact with surface structures such as polarization beamsplitters, grating couplers and integrated phase-sensitive devices.

In a sixth embodiment of the present invention, a gallium indium phosphide, gallium aluminum arsenide or gallium arsenide quantum well active layer or other active layer providing lasing output in the 635 nm to 850 nm wavelength range is fabricated on suitable substrate material. A barrier layer, a cladding layer, a reducing layer and a contact layer are positioned on top of the active layer. In the region of surface sensitivity, the cladding layer has a thickness less than 0.5 microns and the thicknesses of the reducing layer and the contact layer are reduced, perhaps to where the reducing and the contact layers are not present. Two stripe electrodes are positioned over the thin p+-GaAs contact layer such that the laser can be operated under voltage applied to either electrode or to both electrodes. Operation of the twin stripe laser is dependent on the refractive index, absorption and scattering characteristics of the material between the stripes. The stripes can also be segmented coupled stripes with a gap between the segments.

These and further and other objects and features of the invention are apparent in the disclosure, which includes the above and ongoing written specification, with the claims and the drawings.

BRIEF DESCRIPTION OF THE DRAWINGS

FIG. 1 is a schematic side view of a semiconductor diode laser sensor having a segmented electrode and a surface active region.

FIG. 2 is a schematic side view of a semiconductor diode laser sensor having a segmented electrode, a surface active region and an intermediate layer positioned over the contact layer in the surface active region.

FIG. 3 is a schematic plan view of an integrated surface-active laser diode sensor.

FIG. 4 is a schematic cross-sectional illustration of an integrated surface-active laser diode sensor.

FIG. 5 is a plan view of one embodiment of a laser diode sensor having a segmented electrode, a thin gold coating in the surface active region, and a buffer layer between the coating and the contact layer.

FIG. 6 is a side illustration of the embodiment of FIG. 5.

FIG. 7 shows a laser diode sensor having a pair of segmented electrodes.

FIG. 8 shows a laser diode sensor having unsegmented electrodes and a detector region connected to the laser structure.

DETAILED DESCRIPTION OF THE PREFERRED EMBODIMENTS

Referring to FIG. 1, a range of sensors 1 based on semiconductor diode lasers have surface active regions. A laser structure 3 is constructed on a suitable substrate material 5.

Preferably, the lasing structure 3, has an active layer 7, barrier layers 11, cladding layers 9 and reducing layers 13. In preferred embodiments of the present invention, the active layer 7, is a quantum well structure comprised of gallium indium phosphide layer, a gallium aluminum arsenide layer or combinations thereof. A contact layer 15 is deposited on the on the reducing layer 13 in regions away from the surface active region. In preferred embodiments of the present invention, the cladding layer 9 is comprised of p-doped aluminum indium phosphide or gallium aluminum arsenide contact layer having a thickness of less than 0.5 microns in the surface active region. At least one electrode 19 is positioned on the contact layer 15. The electrode can be a stripe electrode. FIG. 1 shows a preferred embodiment of the present invention having a segmented electrode 19. The segmented electrode 19 has a first contact pad 21, a second contact pad 23, and a gap 25 between the first pad 21 and the second pad 23. That gap 25 functions as the surface active area of the sensor 1. The surface active area 25, the contact pads 21, 23 or both can be coated with a chemically sensitive material. The laser structure 3 generates a signal. The tail of the lasing mode is effected by the chemical environment present in the surface active area 25. The output 27 of the laser structure 3 reflects those effects on the generated signal. The laser output 27 exits through an output mirror 29 and is detected by a detector region 31.

As shown in FIG. 2, the surface active area 25 is coated with an intermediate layer 33 or with a chemically sensitive material that may be a polymer, a polymer containing a chemically sensitive material such as an absorbing dye, a polymer containing a fluorophore, a thin ceramic layer containing a fluorophore or any combination thereof. A metallic layer can be used to excite the surface plasmon effect. The chemically sensitive material exhibits a change in refractive index, spectral optical density, fluorescence, or thermal or electrical property when exposed to an analyte. The change in the chemically sensitive material is detected as a corresponding change in laser amplitude, modulation characteristics, threshold current or voltage, operating current/voltage characteristics, polarization, wavelength, self-pulsation frequency, self-pulsation amplitude, phase, mode structure, beam direction or other measurable feature.

Several embodiments of the present invention are shown in the figures.

FIG. 3 is a plan view of a surface active semiconductor diode laser sensor 1 having a gold top segmented electrode 41 with a surface active region 43. The sensor 1 has a p-doped GaAs contact layer 45 having a thickness of 0.2 microns or less deposited over the laser structure. The gap, or surface active, region 43 between the two segments or pads 47, 49 forming the electrode 41 is coated with a material 51, such as an absorbing dye having a spectral absorbance changing as a function of external pH or having spectral characteristics that are a function of the chemical environment. The output 53 of the diode laser sensor 1 is a function of the absorbance of the material at the laser wavelength. In preferred embodiments such as shown in FIG. 3, the sensor 1 has a length 52 ranging from one to two millimeters and the electrode 41 has a width 54 ranging from four to twenty microns. Preferably, the electrode 41 ranges from 0.3 to 0.6 microns in thickness, and the distance between the pads 47, 49 of the electrode 41 is approximately 100 microns.

FIG. 4 is a cross-sectional front schematic illustration of the surface active laser diode sensor 1 taken through the surface active region. A laser structure 63 having an active layer 65 and cladding layers 67 is constructed on a substrate 69. A thin contact layer 71 is positioned on the upper surface of the laser structure 63. A metallization or oxide layer 73 overlies the contact layer. An additional metallization layer 75 can be applied to the underside of the substrate. Preferably, the contact layer 71 is a p-doped GaAs layer, and the substrate 69 is an n-GaAs substrate. The surface-active area can be doped or can be coated with a chemically sensitive sol-gel or semiconductor layer.

FIGS. 5 and 6 show an embodiment of the present invention having a segmented electrode 19 positioned over a thin p-clad GaAs contact layer 15. The surface active area 25 between the contact pads 21, 23 of the segmented electrode 19 is coated with a thin gold coating 81. In preferred embodiments, the coating 81 is between 30 nm and 50 nm thick. Preferably as shown in FIG. 6, a thin layer 83 separates the gold coating 81 from the contact layer 15. That thin layer 83 serves as a buffer layer and a tuning layer. In preferred embodiments of the present invention, the thin layer 83 is a silica, titania or alumina layer. The segmented electrode 19 can also be coated by a chemically sensitive polymer as a surface layer.

FIG. 7 shows another embodiment of the present invention. Two pairs of segmented electrodes 91, 93 are positioned over a p-GaAs surface layer 95. Each segmented electrode 91, 93 has a first contact pad 97, a second contact pad 99 and a surface active area 100 between the first and second contact pads. In preferred embodiments, the pads 97, 99 of the segmented electrodes 91, 93 are spaced more than 100 microns part. One segmented electrode 91 functions as a reference. A protective coating 103 is deposited in the gap region 101 between the contact pads 97, 99 of the reference electrode 91 to prohibit interaction with the analyte. The region 105 between the contact pads 97, 99 of the other electrode 93 is left unprotected and thus may interact with the analyte. Both the protected region 101 and the unprotected region 105 provide lasing action, thereby allowing sensitive discrimination of the effects of the analyte.

FIG. 8 shows another embodiment of the present invention having two unsegmented electrodes 111, 113 positioned over the p-GaAs contact layer 115. The electrodes 111, 113 are spaced less than 10 microns apart to provide a coupled laser mode. An absorbing dye, a fluorophore, or a material exhibiting a change in refractive index is deposited in the active region 117 between the two electrodes 111, 113 to provide a change in laser output. The sensor 110 has a detector region 121 that contains optical or optoelectronic components 123. As shown in FIG. 8, the detector region 121 may be integral with the surface of the diode laser. Possible optical components for use in the present invention include lenses, gratings, beamsplitters, polarization beamsplitters, photodetectors, interferometers, heaters, nonlinear optical components or other components.

Preferred embodiments of the present invention have a p-GaAs contact layer and a n-GaAs substrate. Alternatively, the present invention can be built using a thin n- cladding layer with a p+ substrate. Further, any composition that produces a gain region in the semiconductor material can be used if appropriate steps are taken to allow evanescent interaction of the laser gain region with the coating or with the environment. A distributed Bragg grating can be used in place of the Fabry Perot cavity structures shown in the figures without any loss of generality. When a distributed Bragg grating is used as a front and back reflector of the laser structure, the sensor can include integral photodiodes, a polarization beamsplitter, an interferometer or the like. When lithography is used to prepare a gap between the output mirror of the structures, and when the mirror is fashioned using fabrication processes involving semiconductor material deposition or deposition of suitable dielectric or metallic materials, a semiconductor photodiode, a semiconductor electrode, a polarization beamsplitter, an interferometer or other optical component can be positioned in the region beyond the output mirror to provide a totally integrated sensor structure.

The present invention can use an optically excited or electronically excited laser amplifier without any loss in generality. Multiple sensors can be joined together by adding additional segmented or unsegmented electrodes. The additional electrodes can be separated by distances less than 10 microns to allow coupled mode interaction and interference, and by distances greater than 100 microns to allow separate reference channels to be configured.

While the invention has been described with reference to specific embodiments, modifications and variations of the invention may be constructed without departing from the scope of the invention, which is defined in the following claims.

We claim:
1. A surface-active laser chemical sensor for detecting chemical changes in an ambient environment comprising a substrate, a diode laser structure deposited on the substrate for generating a laser signal, the laser structure further comprising an active layer, a barrier layer on the active layer, a cladding layer on the barrier layer, and a reducing layer on the cladding layer, a contact layer formed on the reducing layer having a deposited electrode, a surface sensitive region adjacent to the electrode, wherein in the surface sensitive region the thickness of the cladding layer is from 0.5 microns to less than 0.05 microns to enable a tail of a lasing mode to have a finite value at the surface of the laser, such that the laser structure and the signal generated by the laser structure exhibit sensitivity to an analyte at the surface sensitive region, wherein the laser structure produces in the presence of the analyte a laser signal, and wherein the laser signal is detected by a detector.

2. The apparatus of claim 1, wherein the detector is integrated with the laser structure.

3. The apparatus of claim 1, wherein the detector is external to the laser structure.

4. The apparatus of claim 1, wherein the active layer in the laser structure lases at a wavelength where the analyte has an absorption peak.

5. The apparatus of claim 1, wherein the intermediate layer is selected from the group consisting of silica, alumina and titania.

6. The apparatus of claim 1, wherein the first electrode is a single gold contact pad.

7. The apparatus of claim 1, wherein the substrate is a n-GaAs substrate, and wherein the cladding layer is a p-gallium indium phosphide cladding layer.

8. The apparatus of claim 1, wherein the substrate is a p-GaAs substrate, and wherein the cladding layer is a n-gallium indium phosphide cladding layer.

9. The apparatus of claim 1, further comprising a coupling structure formed of a distributed mirror, and an optical component provided in a region spaced from the distributed mirror (Bragg reflector), the optical component being selected from the group consisting of a semiconductor photodiode, an electrode, an optical coupler, a beam splitter, a polarization beamsplitter or an interferometer.

10. The apparatus of claim 1, further comprising a fluorescent material deposited in a carrier over the cladding layer, and wherein the active layer in the laser structure lases at a wavelength where the fluorescent material deposited over the cladding layer has an absorption peak in the presence of the analyte.

11. The apparatus of claim 1, wherein the active layer in the laser structure has a composition that allows lasing between 700 and 880 nm.

12. The apparatus of claim 1, wherein the active layer of the laser structure lases between 630 nm and 700 nm.

13. The apparatus of claim 12, wherein the active layer is gallium indium phosphide.

14. The apparatus of claim 1, wherein the active layer of the laser structure has a composition that allows lasing between 630 nm and 700 nm.

15. The apparatus of claim 14, wherein the active layer is a quantum well active layer and has a composition comprising gallium indium phosphide.

16. The apparatus of claim 1, wherein the cladding layer is gallium indium phosphide.

17. The apparatus of claim 16, wherein the cladding layer is less than 0.5 microns thick.

18. The apparatus of claim 1, wherein the surface sensitive region has at least one additional optical component integrated in the laser structure.

19. The apparatus of claim 18, wherein the optical component is selected from the group consisting of lenses, gratings, beamsplitters, polarization beamsplitters, photodetectors, interferometers, heaters and nonlinear optical components.

20. The apparatus of claim 1, wherein the cladding layer has a surface corrugation.

21. The apparatus of claim 20, wherein the electrode extends over the area where the cladding has a surface corrugation, and wherein the electrode comprises optical components selected from the group consisting of photodiodes, polarization beamsplitters, and interferometers.

22. The apparatus of claim 1, wherein the electrode is a segmented electrode, the segmented electrode further comprising a first pad and a second pad, and wherein the surface sensitive region is positioned between the first and second pads.

23. The apparatus of claim 22, further comprising an intermediate layer deposited over the surface sensitive region between the pads, the intermediate layer being sensitive to the presence of the analyte and comprising an absorbing dye or a fluorescent dye immobilized in a polymer or ceramic material such that the absorbance or fluorescence or refractive index of the dye/polymer or dye/ceramic material system is altered in the presence of the analyte.

24. The apparatus of claim 22, wherein the first pad and the second pad of the segmented electrode are metal pads.

25. The apparatus of claim 22, further comprising a gold layer deposited over the cladding layer in the surface sensitive region between the pads.

26. The apparatus of claim 25, further comprising a nafion layer deposited over the gold layer.

27. The apparatus of claim 22, further comprising a fluorophore carrier deposited over the surface sensitive region between the pads.

28. The apparatus of claim 27, wherein the fluorophore carrier is selected from the group consisting of a polymer, a sol-gel and a thin-film deposited binder.

29. The apparatus of claim 1, wherein the first electrode is a stripe electrode, and further comprising a second stripe electrode deposited on the contact layer such that the laser can be operated under voltage applied to either electrode or to both electrodes.

30. The apparatus of claim 29, wherein the first electrode and the second electrode are both segmented electrodes having first segments, second segments, and gaps between the first segments and the second segments.

31. The apparatus of claim 30, further comprising a protective coating deposited over a gap between a first segment and a second segment of the second electrode to prohibit interaction with the analyte.

32. The apparatus of claim 29, wherein the first electrode and the second electrode are unsegmented electrodes, wherein the first electrode is substantially parallel to the second electrode, and wherein a surface active region is formed between the first electrode and the second electrode.

33. The apparatus of claim 32, wherein the first electrode and the second electrode are spaced less than 10 microns apart.

* * * * *